(12) United States Patent
Ngo et al.

(10) Patent No.: US 7,579,459 B2
(45) Date of Patent: Aug. 25, 2009

(54) ACTIVATOR BOUND SOLID SUPPORTS FOR NUCLEIC ACID SYNTHESIS VIA THE PHOSPHORAMIDITE APPROACH

(76) Inventors: Nam Q. Ngo, 4191 Rincol Ave., Campbell, CA (US) 95008; Laurent Jaquinod, 3143 Wood Cir., Davis, CA (US) 95616

( * ) Notice: Subject to any disclaimer, the term of this patent is extended or adjusted under 35 U.S.C. 154(b) by 451 days.

(21) Appl. No.: 11/301,020

(22) Filed: Dec. 12, 2005

(65) Prior Publication Data

US 2007/0135626 A1 Jun. 14, 2007

(51) Int. Cl.
*C07H 21/00* (2006.01)
(52) U.S. Cl. ............... 536/25.3; 536/25.32; 536/25.33; 536/25.34; 536/25.31
(58) Field of Classification Search ............ None
See application file for complete search history.

(56) References Cited

U.S. PATENT DOCUMENTS

| | | | |
|---|---|---|---|
| 4,415,732 | A | 11/1983 | Caruthers et al. |
| 4,458,066 | A | 7/1984 | Caruthers et al. |
| 4,725,677 | A | 2/1988 | Koster et al. |
| 5,262,530 | A | 11/1993 | Andrus et al. |
| 5,442,106 | A | 8/1995 | Zeldin et al. |
| 6,090,934 | A | 7/2000 | Kumar et al. |
| 6,590,092 | B1 | 7/2003 | Ngo |
| 6,642,373 | B2 | 11/2003 | Manoharan et al. |

OTHER PUBLICATIONS

Crea et al. Nucleic Acid Research (1980), vol. 8, pp. 2331-2348.*
Azhayev, A. V., "A New Universal Solid Support for Oligonucleotide Synthesis", Tetrahedron 55 (1999), pp. 787-800.
Azhayev et al., "Amide group assisted 3'-dephosphorylation of oligonucleotides synthesized on universal A-supports", Tetrahedron 57 (2001), pp. 4977-4986.
Eleuteri et al., "Pyridinium Trifluoroacetate/N-Methylimidazole as an Efficient Activator for Oligonucleotide Synthesis via the Phosphoramidite Method", Organic Process Research & Development 2000, 4, pp. 182-189.
Fourrey et al., "Improved Procedure for the Preparation of Deoxynucleoside Phosphoramidites: Arylphosphoramidites as New Convenient Intermediates for Oligodeoxynucleotide Synthesis", Tetrahedron Letters 25 (1984), pp. 4511-4514.
Fourrey et al., "A New Method for the Synthesis of Branched Ribonucleotides", Tetrahedron Letters 28 (1987), pp. 1769-1772.
Luz et al., "The Influence of the Diluent System on the Porous Structure Formation of Copolymers Based on 2-Vinylpyridine and Divinylbenzene. Diluent System.III.Heptane/Methylethylketone," Journal of Applied Polymer Science 91 (2004), pp. 666-669.
Nishimura et al., "Ruthenium(II)-Bypyridine Anchored Montmorillonite-Catalyzed Oxidation of Aromatic Alkenes with tert-Butyl Hydroperoxide", Tetrahedron Letters 39 (1998), pp. 4359-4362.
Riedmiller et al., "Synthesis, Properties, and Structure of Poly(silyl)pyridines. The Phantom of Intramolecular Si-N Bonding", Organometallics 1998, 17, pp. 4444-4453.
Santa Maria et al., "Microscopic analysis of porosity of 2-vinylpyridine copolymer networks", Materials Letters 58 (2004), pp. 563-568.
Zeldin et al., "Synthesis and Characterization of Pyridinyldisiloxanes and their Bis-N-Oxides", Journal of Organometallic Chemistry 326 (1987), pp. 341-346.

* cited by examiner

*Primary Examiner*—Patrick T Lewis
(74) *Attorney, Agent, or Firm*—Schneck & Schnek; Thomas Schneck

(57) ABSTRACT

The present invention relates to improved methods for the preparation of nucleic acids. More particularly, conventional solid supports used for nucleic acid synthesis are derivatized with activators having pKas within the 4 to 7 range. Preferentially, CPG-based solid supports are reacted with trialkoxysilanes containing an activator moiety such as pyridine. During each deblocking step of the nucleic acid synthesis cycle, bound pyridiniums are generated, yielding a weak acidic medium spreads throughout the solid support. The bound activators efficiently activate the phosphoramidite reagents towards coupling with 5'-hydroxynucleosides bound to the solid supports, thus eliminating or supplementing external deliveries of activator during the coupling steps.

19 Claims, 4 Drawing Sheets

Activator Bound Solid Supports for Nucleic Acid Synthesis via the Phosphoramidite Approach NGO, Q. N. and JAQUINOD, L.

ACTIVATOR BOUND SOLID SUPPORTS FOR NUCLEIC ACID SYNTHESIS VIA THE PHOSPHORAMIDITE APPROACH

REFERENCES CITED

U.S. Patent Documents

| | | | |
|---|---|---|---|
| 4,415,732 | November 1983 | Caruthers et al. | 536/27 |
| 4,458,066 | July 1984 | Caruthers et al. | 536/25 |
| 4,725,677 | February 1988 | Koster et al. | 536/25 |
| 5,262,530 | November 1993 | Andrus et al. | 536/25 |
| 5,442,106 | August 1995 | Zeldin et al. | 562/512 |
| 6,090,934 | July 2000 | Kumar et al. | 536/25 |
| 6,590,092 | July 2003 | Ngo. | 536/25 |
| 6,642,373 | November 2003 | Manoharan et al. | 536/25 |

Other References

Azhayev, A. V., *Tetrahedron* 1999, 55, 787-780.
Azhayev, A. V. and Antopolsky, M., *Tetrahedron* 2001, 57, 4977-4986.
Eleueri, A., et al., *Org. Process Res. Dev.* 2000, 4, 182-189.
Fourrey, J. L, Varenne, J., *Tetrahedron Lett.* 1984, 25, 4511-4514.
Fourrey, J. L., Varenne, J., Fontaine, C., Guittet, E., Yang, Z. W., *Tetrahedron Lett.* 1987, 28, 1769-1772.
Luz, C. T. L., Coutinho, F. M. B. *J. Appl. Polymer Science* 2004, 91, 666-669.
Nishimura, T.; Onoue, T.; Ohe, K.; Tateiwa, J.-I.; Uemura, S., *Tetrahedron Lett.* 1998, 39, 4359-4362.
Riedmiller, F.; Jockish, A.; Schmidbaur H., *Organometallics* 1998, 17, 4444-4453.
Santa Maria, L. C., Aguiar, A. P, Aguiar, M. R. M. P., Jandery, A. C., Guimaaraes, P. I. C., Nascimento, L. G. *Materials Letters* 2004, 58, 563-568.
Zeldin, M.; Xu, J.-M., Tian, C. -X., *J. Organometallic Chem.* 1987, 326, 341-346.

BACKGROUND OF THE INVENTION

The most commonly used process in nucleic acid synthesis employing solid phase chemistries is the phosphoramidite approach. 5'-Hydroxynucleotides, bound to a polymeric carrier, is phosphitylated with 3'-(β-cyanoethyl-N,N-diisopropylphosphoramidite)nucleosides activated by protonation with weak acids. Acids and amidites are used in excess relatively to the bound nucleotides to ensure a rapid and complete formation of the internucleotide phosphotriester linkage. Phosphoramidite reagents have been activated by addition of tetrazole (pKa 4.9), dicyanoimidazole (pKa 5.2), or pyridinium salts (pKa=5.2-5.5). Other activating agents has been used such as 5-trifluoromethyl-1H-tetrazole, 5-ethylthio-1-H-tetrazole, 5-benzylthio-1-H-tetrazole, 2,4,5-tribromoimidazole, 2-nitroimidazole, 1-hydroxy-benzotriazole, 5-chlorobenzotriazole, and benzimidazolium, imidazolium, pyridinium, N-methylimidazolium, N-methylanilinium trichloroacetate salts. References related to those activators can be found in Eleueri et al., Organic Process Research & Development 2000 and U.S. Pat. No. 6,642,373.

In automated nucleic acid synthesizers, amidite and activator solutions are delivered successively to the solid supports. Poor mixing of the two solutions lead to lower phosphitylation yields and a growing accumulation of sequence failures by failing to activate the amidites. Trends towards higher throughput and lower synthesis scale (i.e., 1 to 20 nmols) accentuate this drawback as smaller volume of reagents are being delivered to the solid supports. To minimize or eliminate these drawbacks, we anchored activator moieties to the polymeric carriers commonly used in the solid phase synthesis of nucleic acids. The said activators have pkas in the 4 to 7 range and are being reprotonated (i.e. regenerated) during each detritylation step, prior to the phosphitylation step (vide infra).

BRIEF SUMMARY OF THE INVENTION

The present invention relates to the modification of solid supports for nucleic acid synthesis with covalently bound activators having pKas in the 4 to 7 range, preferentially in the 5 to 6 range. The said supports consist of an organic carriers (such as cross-linked polystyrene) or inorganic carriers (such as controlled pore glass, silica, quartz wafers) which possess pre-attached nucleosides protected with p,p'-dimethoxytrityl groups or pre-attached universal linkers to provide sites for oligonucleotide construction.

The said activator bound solid supports are compatible to the existing methods of automated nucleic acid synthesis employing 5'-O-dimethoxytrityl protected nucleoside phosphoramidites. Oligonucleotides are synthesized through repeated cycles of deprotection and coupling. A cycle comprises four steps each: (a) 5'-dimethoxytrityl group deblocking, (b) amidite coupling catalyzed by an activator, (c) oxidation of the internucleotide phosphite linkages to phosphate linkages and, (d) capping of unreacted 5'-hydroxy groups. The four step cycles is repeated until the bound-oligonucleotides reach their full length. In the inventive supports, step (a) simultaneously results in 5'-dimethoxytrityl deblocking and in (re)protonating the activator moieties bound to the solid support. Preferentially, the said solid supports are derivatized with covalently bound pyridine moieties (FIG. 1). Step (b) can take place without delivery of an external activator as the bound activator can efficiently catalyze the amidite couplings. Bound-activators effectively replace or supplement an external addition of activator in the cases of a poor mixing of reagents or a failed activator delivery. This novel strategy optimizes the internucleotide bond formation via the phosphoramidite approach and offers entries to very small-scale syntheses of nucleic acids. The present invention makes the nucleic acid synthesis less prone to early termination.

Some of the terms employed in the present description are defined subsequently, after which the invention is explained in detail. The term "nucleic acid" refers to single stranded chain of either ribonucleic acid or deoxyribonucleic acid or oligonucleotide having from two to several hundred nucleotides. Base labile-protective groups are those conventionally employed in the chemical synthesis of nucleosides, nucleotides and oligonucleotides (see, for example: Protocols for Oligonucleotides and Analogs, Synthesis and Properties, edited by Sudhir Agrawal, Humana Press, Totowa, N.J.). Phosphoramidite chemistry is taught in U.S. Pat. Nos. 4,725, 677, 4,458,066 and 4,415,732. Universal linkers are used to synthesize nucleic acids regardless of the nature of their 3'-or a 5'-terminal base by reacting selectively with the 5'-or a 3'-end of a nucleoside functionalized in particular with a phosphoramidite moiety and depending on whether the synthesis is carried out in the 5' to 3' or 3' to 5' direction. We described catechol-based universal linkers in U.S. Pat. No. 6,590,092. Aliphatic vicinal-diol based universal linkers are described in U.S. Pat. No. 6,090,934 and by Azhayev (1999, and 2001) and references therein.

DETAILED DESCRIPTION OF THE INVENTION

Nucleic acids are synthesized on automated workstations upon selection of appropriate solid supports containing a universal linker or a protected nucleoside covalently attached to a polymer carrier. In the present invention, the said solid supports for nucleic acid synthesis have been further derivatized with an amidite activator. The present invention relates to the modification of the said solid supports with covalently bound activators having pKas in the 4 to 7 range, preferentially in the 5 to 6 range. The said supports consist of conventional organic carriers (such as cross-linked polystyrenes) or an inorganic carriers (such as controlled pore glass, silica, quartz wafers) which possess pre-attached nucleosides or pre-attached universal linkers to provide a site for oligonucleotide construction. The resulting activator bound solid supports can be used to synthesize oligonucleotides by means of phosphoramidite reagents without resorting to an external addition of an activator.

The said activator bound solid supports in accordance with some embodiments of the present invention have the following formulae A-L1-W-L2-Y wherein:

W is a polymer carrier that may be selected from inorganic polymers such as silica gel (porous or non-porous), controlled pore glass (CPG) and, quartz wafers or from organic polymers. It is possible to use soluble or insoluble (that is to say crosslinked) organic polymer carriers, for example polyester, polyamide, polyvinyl alcohol, polystyrene or the like.

A is an activator moiety. A useful activator contains one or more protonation sites having pKas in the 4 to 7 range, preferentially in the 5 to 6 range.

L1 is a (C, H, N, O) containing linker arm covalently attaching the activator (A) to the polymer carrier W.

Y is a moiety containing a reactive site for nucleic acid synthesis. Preferably, Y contains a hydroxyl group that may be protected with a dimethoxytrityl group. Specific examples of Y include, but are not limited to, a nucleoside attached to the carrier W via the 3'-end or 5'-end of its sugar ring, a universal linker or linkers containing dyes (TAMRA, fluorescein and the like).

L2 is a (C, H, N, O) containing linker arm covalently attaching Y to the polymer carrier W. Ester or thioester or carbamate linkages are preferred for the attachment of Y moieties to W and can be cleaved under basic conditions.

Preferably, L1 and L2 represent a straight or a branched C2 to C18-alkylene group or an alkylene group interrupted by a heteroatom such as oxygen, sulfur, N-alkyl or other N-substituted nitrogen atom.

Figure 2:
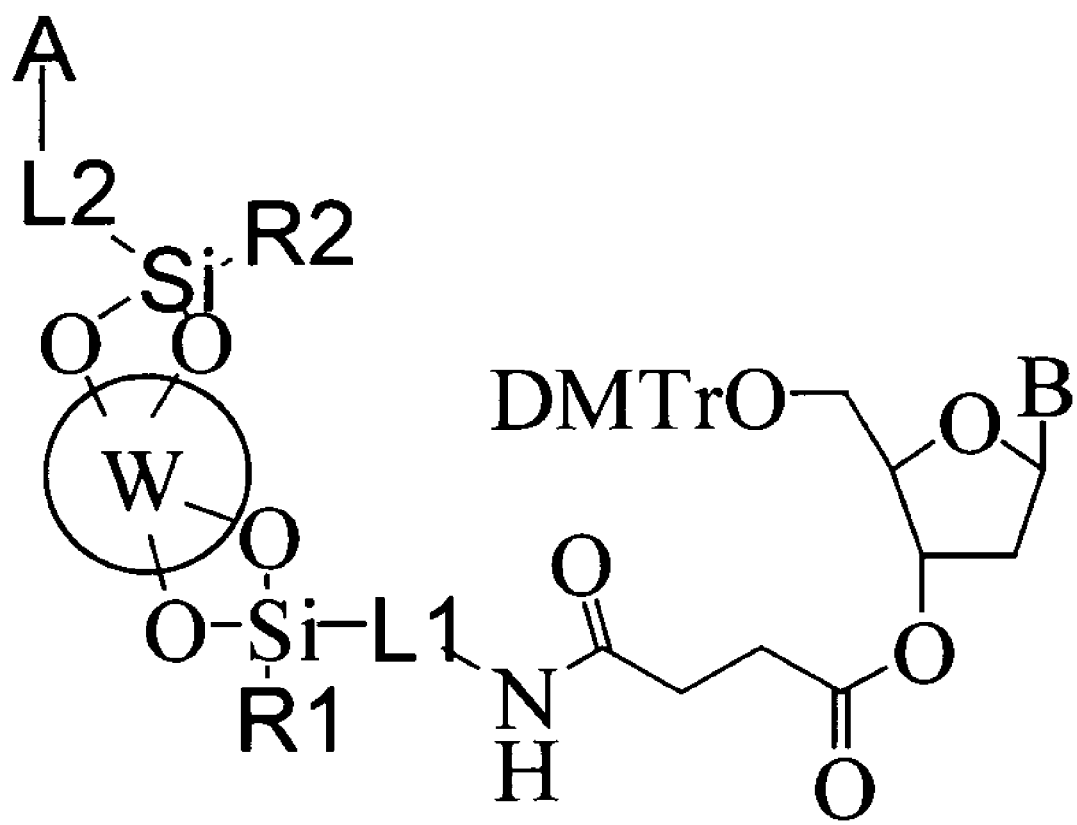
FIG. 2 describes the schematic structure of a CPG based solid support derivatized with a bound activator A.
Figure 3:
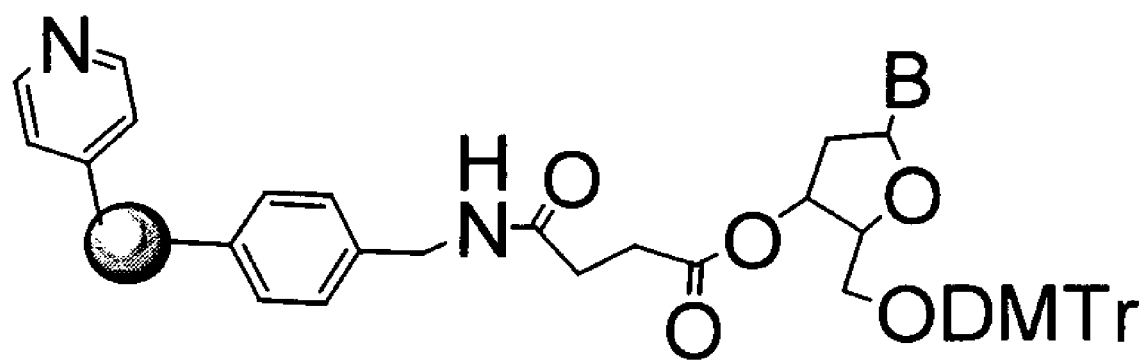
FIG. 3 describes the schematic structure of a cross-linked PS-DVB based solid support containing pendant pyridine moieties.

In a particularly preferred embodiment, activators are covalently bound to controlled porous glass (CPG) which structures are shown FIG. 2, wherein:

A is an activator moiety with one or more protonation sites having pKa within the 4 to 6 range. Specific examples of multiprotic activator are bipyridine, terpyridine.

B is a nucleoside base selected from the group consisting of adenine, guanine, cytosine, thymine, uracil and analogs thereof which are protected by acyl groups or Schiff bases.

L1 and L2 represent a straight or a branched C2 to C18-alkylene group or an alkylene group interrupted by a heteroatom such as an oxygen or sulfur.

R1 and R2 are selected from the group consisting of methoxy, ethoxy, methyl, ethyl, and the likes.

In a preferred embodiment of this invention, activators are grafted on CPG by using bifunctional silanes, i.e. silanes having a first functional group enabling covalent binding to the CPG surface and a second functional group that imparts the desired chemical modifications to the surface. CPG is commercially available in a variety of sizes. Preferably, the particle sizes are in the 10-300 microns range, and more preferably 75-200 microns. As used herein, porous means that the CPG beads contain pores having substantially similar diameter in the range between 300-3000 angstroms. Preferably, the pore diameters are about 1000 angstroms. Activator derivatized silanes are covered by the general formulae $[(A)L](R)_n(X)_{3-n}Si$, wherein $n=0$ to 2. (X) is an hydrolysable group typically alkoxy, acyloxy, halogen, imidazole or amine. (R) is selected from methyl, ethyl, propyl, phenyl, pyridyl and the like. L represents a C, H, N, O containing alkylene group covalently linking (A) to Si. (A) is a non-hydrolyzable organic radical possessing one or more acidic functions having pKas in the 4 to 7 range, preferentially within 5 to 6. The pKa range for nitrogen containing bases is given for their conjugated acid forms. Examples of (A) are taken from the group of pyridine, bipyridine, terpyridine, quinoline, benzoquinoline, pyrimidine, polypyridine, alkylaniline, dipyridylaniline, dipyridylaminobiphenyl, dialkylaminopyridine, benzimidazole, benzothiazole, benzotriazole, and imidazole.

Silanes containing pyridine (Zeldin et al, 1987, Riedmiller et al, 1998; Fourrey et al 1984, 1987), bipyridine (Nishimura et al, 1998) and quinoline (Riedmiller et al, 1998) have been prepared from their corresponding bromo-derivatives, butyl-lithium and tetraethoxysilane. N-(3-(diethoxy(methyl)silyl) propyl)-N-methyl-4-aminopyridine, N-(3-(triethoxysilyl) propyl)-N-methyl-4-aminopyridine and bis-silane such as N,N[bis(3-(triethoxysilyl)propyl)]-4-aminopyridine have been described in U.S. Pat. 5,442,106.

Preferred silanes are 2-(4-pyridylethyl)trialkoxysilane, 2-(trialkoxysilylethyl)pyridine, and N-(phenylaminomethyl)trialkoxysilane. In one preferred embodiment, nucleoside-bound CPG (5-50 µmol/g, 1000 angstrom, 75/200) or universal linker bound CPG (5-50 µmol/g, 1000 angstroms, 75/200) are reacted with 2-(4-pyridylethyl)triethoxysilane purchased from Gelest, Inc. The resulting bound pyridine loading is in the 50-200 µmol/g range, as estimated by recovering unreacted silanes. Remaining silanol groups are capped with trisubstituted-silylimidazole or trisubstituted-silylchloride in the presence of pyridine. Trisubstituted-silyl groups include, for example, a trimethylsilyl group, a triethylsilyl group, a t-butyldimethylsilyl group, a dimethylphenylsilyl group, a diphenylmethylsilyl group, and a dimethyl(2-pyridyl)silyl group. Other preferred activator-containing silanes can be prepared by reacting aminoalkyl(trialkoxy)silane with activator-containing carboxylic acids mediated by HATU, DCC, HBTU, PyBop or other coupling agents commonly used in peptide chemistry. Alkoxy are selected from the group consisting of methoxy, ethoxy, propoxy, butoxy, phenoxy and the likes while alkyl is selected from C2 to C18-alkylene groups. Preferred carboxylic acids include those of pyridine, pyrazine, pyrimidine and quinoline. Specific examples of carboxylic acids include nicotinic acid, isonicotinic acid, picolinic acid (2-, 3-or 4-pyridyl)acetic acid, (2-, 3-or 4-pyridine)propionic acid, (4-pyridylthio)acetic acid, (2-pyrimidylthio)acetic acid, (2-, 3-, 4-or 8-)quinolinecarboxylic acids. Based on cost, isonicotinic acid may be used preferentially. N-(3-triethoxysilylpropyl)isonicotinamide is prepared by reacting triethoxysilylpropylamine with isonicotinic acid pre-activated with carbonyldiimidazole in dichloromethane.

In another embodiment, solid supports prepared from alkylaminoalkylCPG or commercially available "long chain alkylamine" CPG (LCAA-CPG) are capped with activator-containing moieties after loading the leading nucleoside or a universal linker. Instead of being acetylated with acetic anhydride, remaining amino groups are preferentially capped with activator-containing carboxylic acids in the presence of HATU, DCC, HBTU, PyBop or other coupling agents commonly used in peptide chemistry. Specific examples of carboxylic acids include nicotinic acid, isonicotinic acid, picolinic acid (2-, 3-or 4-pyridyl)acetic acid, (2-, 3-or 4-pyridine)propionic acid, (4-pyridylthio)acetic acid, (2-pyrimidylthio)acetic acid, (2-, 3-, 4-or 8-)quinolinecarboxylic acids. Capping with activators-containing isocyanates or isothiocyanates or sulfonylchloride groups provide activators bound to the solid support through carbamate or thiocarbamate or sulfonamide linkages, respectively. A specific example of isothiocyanate is 3-pyridyl isothiocyanate. A specific example of sulfonylchloride is 8-quinoline sulfonylchloride.

Other representative solid supports that are amenable to be capped with activator based carboxylic acids include without limitation, copolymers of styrene and divinylbenzene (PS-DVB) and copolymers of vinylpyridine, styrene and divinylbenzene. The said copolymers functionalized with methylamino groups (introduced by reaction with hydroxymethylpthalimide in the presence of methylsulfonic acid and then with hydrazine) are attached to 5'-O-DMTr protected nucleosides through succinate linkers according to procedures described in U.S. Pat. No. 4,458,066 and U.S. Pat. No. 5,262,530. Remaining amino groups are capped with activator based carboxylic acids in the presence of HATU, DCC, HBTU, PyBop or other coupling agents commonly used in peptide chemistry instead of being acetylated. Preferentially, pyridine capped poly(styrene-co-DVB) beads have a 10-50% crosslink ratio, 40-200 micron diameter, pore with diameters of about 1000 angstroms and a pyridine substitution level of 0.1 to 2 mmol/g. Copolymers of vinylpyridine, styrene and DVB at various proportions are well known (Luz, 2001, Santa Maria, 2004). Such copolymers containing 1 to 20% of vinylpyridine (2-, 3-, or 4-vinylpyridine) may be aminomethylated and coupled with 5'-O-DMTr protected nucleosides through succinate linkers. Obviously, many polymer combinations and variations can be used as activator in light of the above teaching.

It is yet a further object to provide solid supports for oligonucleotides synthesis that have been prepared by mixing two or more polymers carriers, wherein the said carriers contain sites for oligonucleotide construction and/or covalently bound activators. In a preferred embodiment, CPG derivatized with a universal linker or an appropriately protected nucleoside is mixed with an activator-containing polymer. Activator bound substitution levels are found in the 0.1 to 3 mmol/g range, preferably within the 0.2 to 1.5 mmol/g range.

In a particularly preferred embodiment, the said activator-containing polymer is an non-water soluble organic copolymer of vinylpyridine or vinyldicyanoimidazole or allylaminoalkylpyridine and styrene and DVB. Preferentially macroporous PS-DVB beads containing 1% to 20% of cross-linked pyridine (from 2-, 3-or 4-vinylpyridine) are used.

Figure 1:
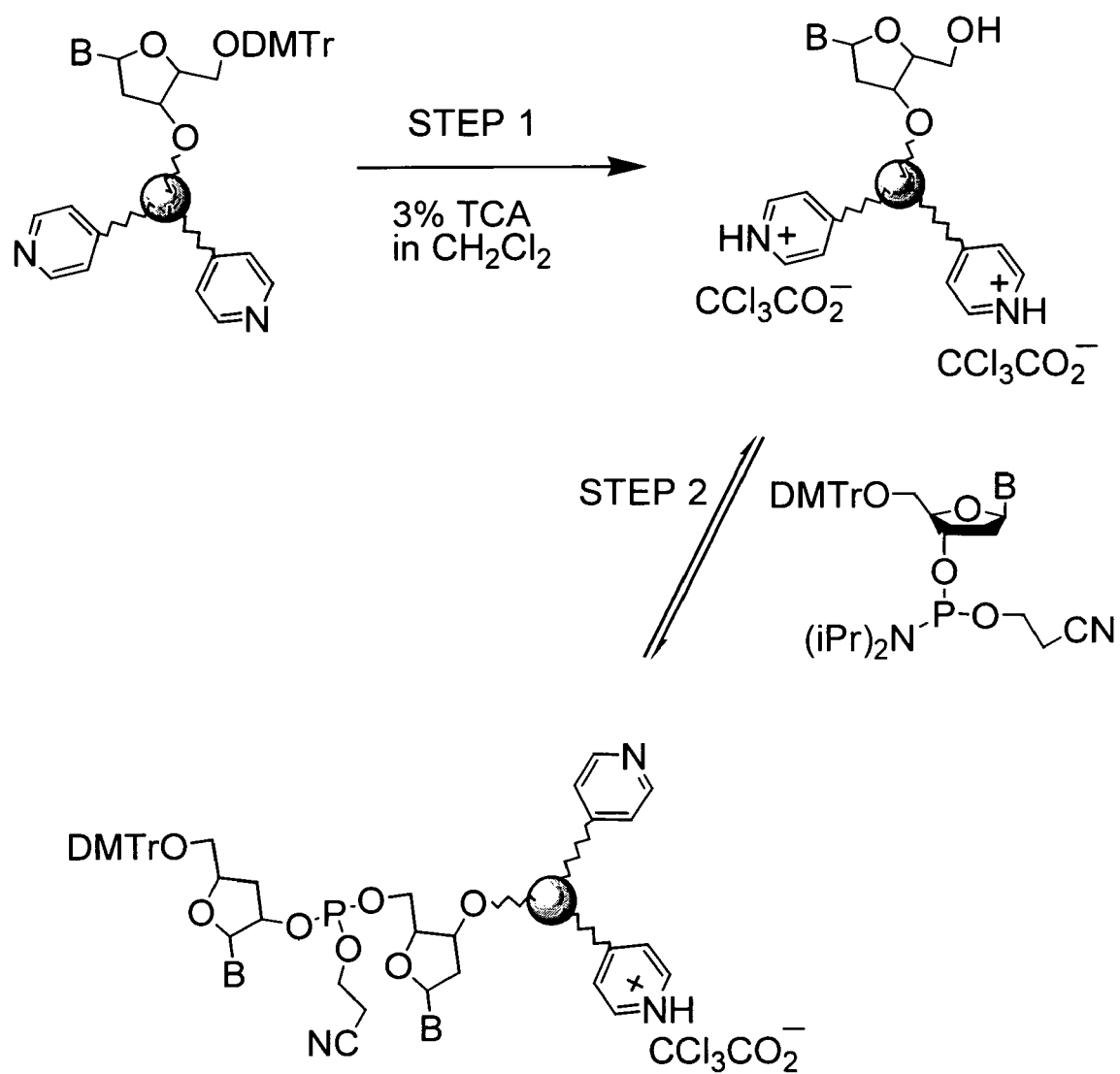
FIG. 1 describes steps (a) and (b) of a nucleic acid synthesis cycle taking place on a pyridine-bound solid support.

It is still a further object of the present invention to provide methods of producing nucleic acids following a phosphoramidite approach by using an activator bound solid support. Phosphoramidite chemistry carried out on automated workstations relies on the successive deliveries of activator and amidite reagents to the solid supports, as known to those skilled in the art. Amidites and activators, which are predissolved in acetonitrile, are stored separately to ensure the stability of the amidite solutions. When activator bound solid supports is used, smaller amount or none of an external activator is needed to activate the amidite reagents during the coupling steps. Preferentially, the said solid supports are derivatized with covalently bound pyridine moieties (FIG. 1). Upon protonation, the resulting bound pyridiniums yield a weak acidic medium equally spreads throughout the solid support. Mechanistic aspects of amidite activation with pyridinium salts, which are known to be good amidite activators, are discussed in U.S. Pat. No. 6,642,373. Oligonucleotides are synthesized through repeated cycles of deprotection and coupling. A cycle comprises four steps each:

(a) A deblocking step: the solid support is treated with a protic acid to cleave the 5'-O-dimethoxytrityl of the bound nucleotides. Deprotecting reagents such as 3% to 5% dichloroacetic acid (pKa 1.29) or 3% trichloroacetic acid (pKa 0.65) in dichloromethane are used. This step ensures the protonation of the bound activator. When a solid support containing a high loading of activator is used, a higher concentration of trichloroacetic acid (TCA) in dichloromethane is required in order to compensate for the acid neutralized by the bound activators while keeping the TCA delivery volume unchanged. As an example, a solid support containing 3 mmol/g of bound pyridine moieties may be detritylated using a 4.5% TCA in dichloromethane.

(b) A phosphitylation step: phosphoramidite-nucleosides are activated by protonation and coupled with 5'-hydroxyoligonucleotides bound to the solid support. Bound activators can be used conjointly with an external activator or as the sole protic source.

(c) An oxidation step: the phosphotriester linkages resulting from the coupling step (b) are oxidized to the corresponding phosphate linkages.

(d) A capping step: unreacted bound 5'-hydroxyoligonucleotides are acetylated to prevent the formation of side products during the subsequent synthesis cycles. Although the synthesis loop is preferentially ended with the capping step, oxidation and capping step order can be inverted. We note that bound pyridines or bound dialkylaminopyridines can catalyze coupling steps and capping steps.

The next cycle starts with step (a), simultaneously cleaving the dimethoxytrityl groups and reprotonating the activator moieties bound to the solid support. The process is repeated until the oligonucleotides reach their full length. Synthetic details regarding steps (a-d) are discussed in the following example, which illustrates the present invention. It is not intended to be exhaustive or to limit the invention to the precise form or reaction schemes disclosed.

EXAMPLE

Nucleic Acid Synthesis Without External Delivery of an Activator During the Coupling Steps $T_5$-TAMRA (SEQ ID 1) is synthesized using TAMRA-CPG (10 µmol/g) wherein TAMRA moieties are attached through a base-labile linkage to the CPG carrier (TAMRA-CPG from CTGen Inc, Milpitas, Calif.). The first TAMRA-CPG support (a) has no bound activator while the second (b) and the third (c) TAMRA-CPG supports have low and high activator loading, respectively. Supports (b) and (c) were prepared by reacting support (a) with 2-(4-pyridylethyl)triethoxysilane (1 mL/10 g CPG in dichloromethane for four hours and two days, respectively. The nucleic acid syntheses are carried out on a 200-nmol scale using an ABI 3900 synthesizer and standard cyanoethylphosphoramidites. Each synthesis cycle consisted of detritylation (3% TCA in $CH_2CL_2$), washing (MeCN), coupling of amidite reagents without external delivery of an activator, washing (MeCN), oxidation (0.02 M iodine in pyridine/$H_2O$/MeCN, 1.5:1.5:7, v/v/v), capping with acetic anhydride in a mixture of pyridine and N-methylimidazole (standard cap A and cap B) and washing (MeCN). The bound pyridine moieties are reprotonated during each detritylation step. 3% TCA in dichloromethane (300 µL) is used. The pyridinium thus obtained are the sole amidite activators. Three µmols of amidites dissolved in acetonitrile are delivered to the pyridinium-bound solid supports and reacted for about 60 s at room temperature.

Figure 4A:
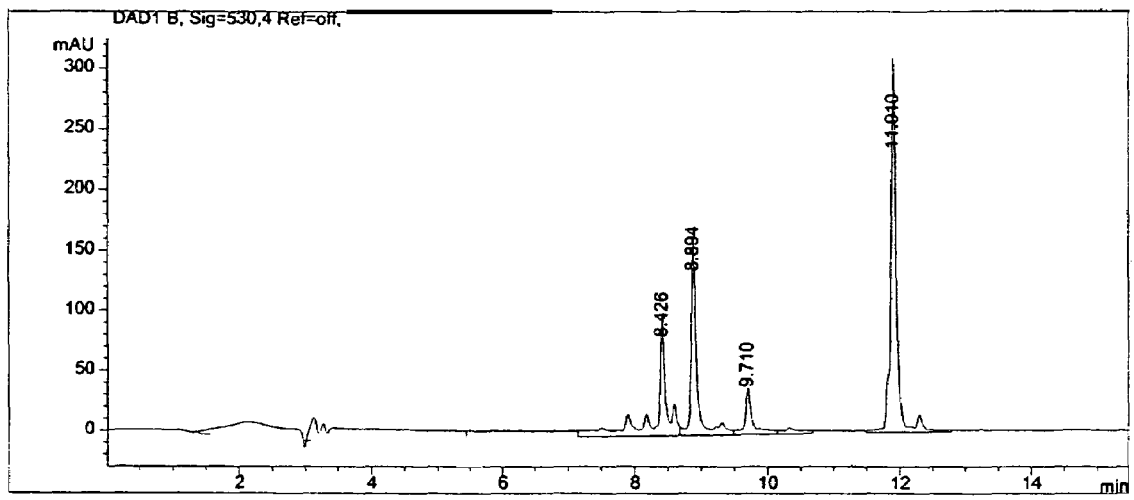
FIGS. 4A and 4B are HPLC chromatograms of DMT-on T5-TAMRA oligonucleotides, synthesized using TAMRA-CPG containing a low loading of bound-activator (A) and, a high loading of bound-activator (B). Coupling steps were carried out without external addition of activator.
Figure 4B:
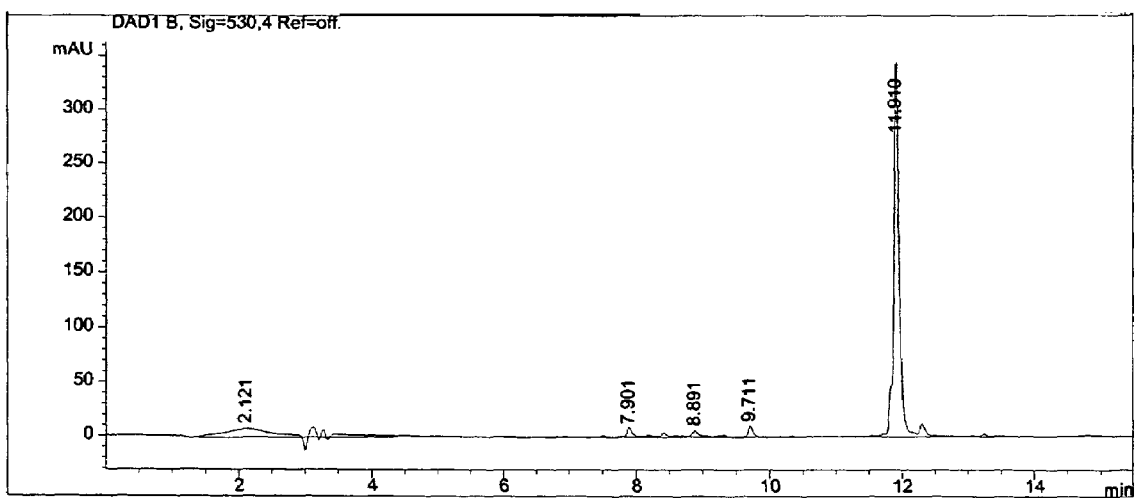

The final step of detachment of $T_5$-TAMRA nucleic acids from the solid supports and removal of the protecting groups is carried out with $tBuNH_2/H_2O$ (1:1, v/v) at 85° C. for one hour. HPLC analyses were carried out using a Phenomenex column (C18 4.6×150 mm, particle size 5 µm). The column was equilibrated in buffer A (0.1M TEAA, pH 7.0) and eluted in a gradient of buffer B ($H_2O$/acetonitrile, 1:3, v/v). Peaks were recorded at 520 nm in order to better appreciate the ratio between full-length oligonucleotides and failures. FIG. 4A shows that a low loading of pyridine moieties resulted in low coupling yields and gave a mixture of TAMRA-oligonucleotides. A higher bound-activator loading gave $T_5$-TAMRA (FIG. 4A). Without bound activator, only a TAMRA-linker peak for was observed (not shown).

What is claimed is:

1. A solid support suitable for nucleic acids synthesis, wherein activators and universal linkers are covalently attached to the same polymer carrier.

2. A solid support suitable for nucleic acid synthesis, wherein activators and 5'-hydroxy protected nucleosides are covalently attached to the same polymer center.

3. A solid support suitable for nucleic acids synthesis, wherein activators and universal linkers are covalently attached to distinct polymer carriers.

4. A solid support suitable for nucleic acids synthesis, wherein activators and 5'-hydroxy protected nucleosides are covalently attached to distinct polymer carriers.

5. A solid support of claim 1, wherein the said universal linkers are covalently attached to the carriers through base-labile linkages.

6. A solid support of claim 2, wherein the said nucleosides are covalently attached to the carriers through base-labile linkages.

7. A solid support of claim 1, wherein the said polymer carrier is controlled porous glass (CPG).

8. A solid support of claim 1, wherein the said polymer carrier is an organic polymer.

9. A solid support of claim 3, wherein one polymer carrier is CPG and another carrier is an organic polymer.

10. A solid support of claim 1, wherein the said activators have pKas within a 4 to 7 range.

11. A solid support of claim 1, wherein the activator substitution levels are within a 0.01 mmol/g to 3 mmol/g range.

12. An activator of claim 10, wherein the said activator is selected from the group consisting of pyridine, bipyridine, terpyridine, polypyridine, quinoline, biquinoline, dialkylaminopyridine, pyrimidine, alkylaniline, dipyridylaniline, dipyridylaminobiphenyl, carbazole, benzimidazole, imidazole.

13. A solid support of claim 8, wherein the said organic polymer is selected from poly(vinylpyridyl-co-styrene), polyvinylpyridine cross-linked with divinylbenzene and poly(vinylpyridyl-co-styrene) cross-linked with divinylbenzene.

14. A process of synthesizing nucleic acids by the phosphoramidite approach using solid supports of claim 1, wherein phosphoramidite reagents are activated by said activators in addition to an external activator during the phosphitylating steps.

15. A process of synthesizing nucleic acids by the phosphoramidite approach using solid supports of claim 1,

---

SEQUENCE LISTING

```
<160> NUMBER OF SEQ ID NOS: 1

<210> SEQ ID NO 1
<211> LENGTH: 5
<212> TYPE: DNA
<213> ORGANISM: Artificial sequence
<220> FEATURE:
<223> OTHER INFORMATION: Dummy test sequence to demonstrate efficiency
      of synthesis via the phosphoramidite approach using an activator
      bound TAMRA solid support

<400> SEQUENCE: 1 ttttt                                                                   5
``` wherein phosphoramidite reagents are activated solely by said activators during the phosphitylating steps.

16. A process of claim 14, wherein the said activators are reprotonated during the deblocking steps of the nucleic acid synthesis cycle taking place prior to the phosphitylating steps.

17. A process of synthesizing nucleic acids by the phosphoramidite approach using solid supports of claim 2, said activators in addition to an external activator during the phosphitylating steps.

18. A process of synthesizing nucleic acids by the phosphoramidite approach using solid supports of claim 2, wherein phosphoramidite reagents are activated solely by said activators during the phosphitylating steps.

19. A process of claim 17, wherein the said activators are reprotonated during the deblocking steps of the nucleic acid synthesis cycle taking place prior to the phosphitylating steps.

* * * * *